(12) United States Patent
Kim

(10) Patent No.: US 8,500,705 B2
(45) Date of Patent: Aug. 6, 2013

(54) APPARATUS FOR COLLECTION AND ANALYSIS OF HUMAN BODY FLUIDS

(75) Inventor: Kyoung Hun Kim, Seoul (KR)

(73) Assignee: Kyungin Metal Industry Co., Ltd., Gyeonnggi-Do (KR)

( * ) Notice: Subject to any disclaimer, the term of this patent is extended or adjusted under 35 U.S.C. 154(b) by 908 days.

(21) Appl. No.: 12/306,978

(22) PCT Filed: Jul. 2, 2007

(86) PCT No.: PCT/KR2007/003205
§ 371 (c)(1),
(2), (4) Date: Dec. 30, 2008

(87) PCT Pub. No.: WO2008/002113
PCT Pub. Date: Jan. 3, 2008

(65) Prior Publication Data
US 2009/0312726 A1    Dec. 17, 2009

(30) Foreign Application Priority Data

Jun. 30, 2006    (KR) .................. 10-2006-0061416

(51) Int. Cl.
*A61M 1/00* (2006.01)
(52) U.S. Cl.
USPC ............... 604/318; 604/27; 604/35; 604/48; 604/65; 604/119; 604/118; 604/317; 604/322; 604/326; 137/205; 141/35; 141/59; 141/65; 141/198; 119/14.46
(58) Field of Classification Search
USPC .................. 604/119, 317, 318, 322
See application file for complete search history.

(56) References Cited

U.S. PATENT DOCUMENTS

| | | | | |
|---|---|---|---|---|
| 6,045,541 A | * | 4/2000 | Matsumoto et al. | 604/313 |
| 6,142,982 A | * | 11/2000 | Hunt et al. | 604/313 |
| 6,755,807 B2 | * | 6/2004 | Risk et al. | 604/319 |
| 2006/0160134 A1 | * | 7/2006 | Melker et al. | 435/7.1 |
| 2007/0185466 A1 | * | 8/2007 | Co | 604/349 |
| 2009/0177176 A1 | * | 7/2009 | Saito | 604/385.29 |

OTHER PUBLICATIONS

The American Heritage® Dictionary of the English Language, Fourth Edition, 2000.*

* cited by examiner

*Primary Examiner* — Michele M Kidwell
*Assistant Examiner* — Ilya Treyger
(74) *Attorney, Agent, or Firm* — Birch, Stewart, Kolasch & Birch, LLP

(57) ABSTRACT

The present invention relates to the analysis apparatus capable of collecting the body fluid such as urine or blood, for embodiment urination and measuring or calculating the specific constituent from the collected body urine, and the apparatus for collecting body fluid capable of using by connecting to the analysis apparatus and its related article, in which the apparatus for collecting and analyzing for the body fluid of a patient consists of the body fluid collecting part and the collecting part case, the apparatus for collecting body fluid consists of the body fluid collecting part, the total tube and adapter, the collecting part is constructed with the absorbing tube, the sensor tube, the cleansing tube and the passage and is attachable/detachable connected to the collecting part, a diaper and pants exclusive for a patient are provided as the related article such that it is convenient to possess and has effects in the urination having no relations to the intention of a patient or in case of unable to use hand or foot by the intention, moreover in using together with a diaper and in nursing acute and chronic patient.

10 Claims, 20 Drawing Sheets

APPARATUS FOR COLLECTION AND ANALYSIS OF HUMAN BODY FLUIDS

TECHNICAL FIELD

The present invention relates to an apparatus for collecting and analyzing the body fluid, and more particularly to an apparatus capable of measuring volume of body fluid excretion of patients, especially urine volume, and analyzing specific constituents of body fluids such as urine and blood, which include urea, Na+, pH, glucose, BUN, Cr, and protein.

BACKGROUND ART

In the present invention, body fluids include all types of liquid phase substances contained in a body of an animal or a human and generally refer to whole blood, lymph, urine, saliva, sweat and the like, however it particularly relate to blood and urine of a human body. Measurement of urine volume of a patient is an important factor for the evaluation of circulating blood volume. A human body gets into a circulatory collapse state due to the direct reduction of circulatory blood volume such as blood loss, burn and so on caused by all kinds of accidents or surgeries, and due to the indirection reduction of circulatory blood volume such as sepsis (blood infection) and heart failure (myocardial infarction, arrhythmia, etc.). When such occurs, small artery contracts regardless of whether the autonomic (sympathetic and parasympathetic) nervous system is under conscious control, and this resultantly affects blood volume to be supplied to every organ in the body In field or clinical experiences, if a patient loses blood a lot because of internal diseases or during accidents/surgeries, he is provided with fluid (Ringer's solution: physiological saline) to prevent the above-described side effects and further to normalize the circulating blood volume. This consequently induces the relaxation in the small artery supplied to the kidney, and prevents necrosis in renal tubule cells. One of the most crucial criteria that shows whether a proper circulating blood volume is restored after the physiological saline was replenished, and whether an adequate volume of blood flow is provided into the kidney is measuring the urine volume. In effect, urine volume is the very first thing medical staffs check in a patient after loss of the circulating blood volume was replenished through the fluid (Ringer's solution). Monitoring an intake with an output of the body, one can evaluate whether or not the kidney is properly functioning and whether a proper volume of the blood is being circulated. Some of specific constituents contained in blood and urine are used as very important criteria for the evaluation of renal function. The present inventor's Korean Patent Application No. 2005-109136 disclosed a quantitative analysis apparatus for measuring the body fluid with which the information for the blood, urine and other body fluid can be obtained and patients can easily urinate for himself without assistance of a sick nurse.

The quantitative analysis apparatus for measuring the body fluid must be equipped a body fluid collecting apparatus for collecting the body fluid.

The body fluid collecting apparatus has been known by a large number of disclosures besides the above patent application. Especially, a variety of collecting apparatus for easily collecting urine from patients capable of urinating have been suggested.

Korean Patent Application Nos. 2000-47602, 2000-58206, 2001-86938, and 2002-44362 filed by the same inventors designed and disclosed a urine collecting apparatus that automatically senses urine, sucks and cleanses the urine with a bidet, even for use with an unconscious patent.

However, the above urine collecting apparatuses showed the following problems in the result of clinical demonstration.

Firstly, it cannot be used in the posture of lying on one's side because it designed to be fixed a urine induction part and sensor. Since the induction part discharging urine and sensor getting a sense of urine are fixed at a case of body fluid collecting part, when patient turn over on his side for preventing a bedsore of patient, the case of body fluid collecting part was also turn over on it side at the same time.

In the body fluid collecting apparatus having such a structure, it had a problem that it is impossible to properly carry out the function of recognizing urine inside of the case of collecting part and inducting it at the induction part to the gravity direction because the induction part and the sensor are fixed in the case of collecting part.

Secondly, it cannot be used in a sitting posture, especially in the state of sitting in wheel chair because the real part of the body fluid collecting part is bulky and a total tube is located in the down part Namely, there is a problem that once a patient seat on the wheel chair, a patient usually takes a sitting posture, but it will make the body fluid collecting being pressed by the perineal region because the real part of the collecting part is bulky as well as the total tube is bended to close the body fluid passage when a patient takes a sitting posture because the total tube has the structure of locating in the lower part of the collecting part.

Thirdly, a patient is hard to use a diaper because the total tube is located under the collecting part.

Namely, there is a troublesome that in order to easily use a diaper, the lower part of the body urine collecting part and a diaper are set right and are punched a hole and then the total tube is pulled out through the hole, since the total tube passes under the body urine collecting part in using together with a diaper to make interference with each other.

Lastly, a patient is hard to deal with the evacuation.

In other words, it is impossible to attach/detach or exchange only the collecting part case separately.

Namely, in case of the collecting part disclosed in the above literature, it has a structure that the lower part of the collecting part opening is contacted around the anal of the perineal region, moreover it has a structure that the total tube is located from the backward part to the lower part of the body urine collecting part.

Accordingly, there is a problem that the whole neighborhood of the body fluid collecting part and the total tube is easily contaminated with the excrement in the patient's evacuation, and after all, as only the body fluid collecting part case cannot separately exchange, the whole of the collecting part comprising the total tube has to replace for washing.

DISCLOSURE

Technical Problem

An object of the present invention which is contrived to solve the above problem, is to provide a apparatus for collecting body fluid in which a body fluid absorbing part and a sensor part can be freely moved.

The object of the present invention can make the body fluid absorbing part and the sensor to freely move in the direction of gravity in the body fluid collecting part case and thus even if a patient put to bed in the lateral side and the front side alternatively in order to prevent bedsore of patient, the function of recognizing and absorbing the body fluid can be perfectly embodied since the body fluid absorbing part and the sensor move together to the same direction of the body fluid which is pooled in the body fluid collecting part to the direction of gravity.

Another object of the present invention is to provide the apparatus for collecting body fluid in which the body fluid collecting part is to form as small and thin as possible to make not to be pressed the prineal region, and the total tube is to locate in the upper part or the back part of the body fluid collecting part case such that the total tube can be embodied a normal function without bending in seating posture.

Another object of the present invention is to provide the apparatus for collecting body fluid capable of using together with a diaper at any time.

The object of the present invention can nurse a patient sanitarily in which a diaper is fixed between the fixing supporting device and the apparatus for collecting body fluid by using the fixing supporting device that the total tube is to locate in the upper part or the back part of the collecting part and the magnetism of the apparatus for collecting body fluid and the magnet is to interact.

Another object of the present invention is to provide the apparatus for collecting body fluid capable of easily washing in which the contamination with the excrement in a patient's evacuation is prevented and even though occurring in the contamination with the excrement, only the case of the collecting apparatus can be easily exchanged.

Moreover, the present invention makes to embody the function by installing various of sensors in order to accomplish the specific object in management of a patient. Namely, by installing a biosensor such as an enzyme sensor, an immunity sensor, a DNA sensor, a cell sensor and a laboratorial chip, the specific constituent of the body fluid (urine, blood) can be measured. In addition, by installing a gas sensor such as a conductive sensor, a piezoelectric sensor, MOSFET (Metal-Oxide-Semiconductor Field Effect Transistor) sensor, an optical fiber sensor, a spectrometry sensor, it can be functioned to alarm the exchange time of a diaper through a buzzer or melody by automatically recognizing the evacuation in using together with a diaper with the quantitative analysis apparatus for body fluid. Moreover, by installing the flowing part electrode sensor instead of the biosensor which connects the flowing part electrode and the collecting part case electrode, such function can be accomplished.

Another object of the present invention and the problem and the solution for accomplishing the object can be aware from the following detailed description of the invention.

Advantageous Effects

The present invention has an effect of accurately recognizing and absorbing the fluid in changing the posture since the sensor part and the flowing body which recognizing and absorbing the fluid move to the same direction even though the fluid move to the direction of gravity.

By such effect, it can be more increased a convenience in carrying as seating on a chair such as wheel chair with the apparatus for collecting body fluid on.

Since the connecting structure of the collecting body and the flowing body constitutes the joint structure, there is no hindrance by the cable as the flowing body locating in the direction of gravity with its own weight and it is possible to freely rotate by the joint structure. Especially, such structure consisting with the joint can intercept the external exposure of the sensor cable which is the structure problem of the prior applied invention such that the defect of the sensor cable damage can be complemented and the defect in durability of the soft tube material can be complemented.

In addition, the present invention has an effect that it can be worn together with a diaper and the body fluid collecting part and the collecting part case are also possible to conveniently exchange and wash as it is attachable/detachable such that it is conveniently used in the nursing and it can prevent fester of a skin by increasing airing in wearing for a long time.

Meanwhile, by installing the gas sensor, it has an effect on automatically recognizing the evacuation and early alarming the diaper exchange time to reduce a nursing manpower as well as preventing the skin damage which occurred in contacting and leaving the excrement for a long time.

The specific constituent of the body fluid can be measured with the biosensor such that it can contribute to a clinical diagnosis and a prognosis management.

With such effects, it is advantageous to maximize its effect in the urination having no relations to the intention of a patient or in case of unable to use hand or foot by the intention, moreover in using together with a diaper and in nursing acute and chronic patient.

BEST MODE

The technical constitution and function of the present invention will be set forth in detail by preferred embodiments of the present invention with reference to the accompanying drawings.

First of all, in order to promote understanding to the invention, it will be explained to a quantitative analysis apparatus of a body fluid connected to the body fluid collecting apparatus of the present invention.

Figure 1:
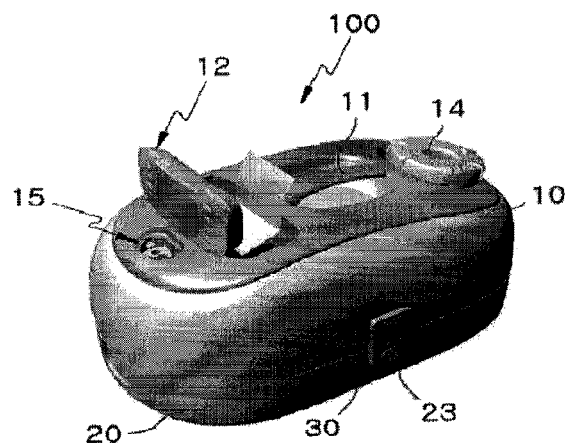
FIG. 1 is a perspective view of the apparatus for analyzing body fluid in which the body fluid collecting part of the present invention is connected.
Figure 2:
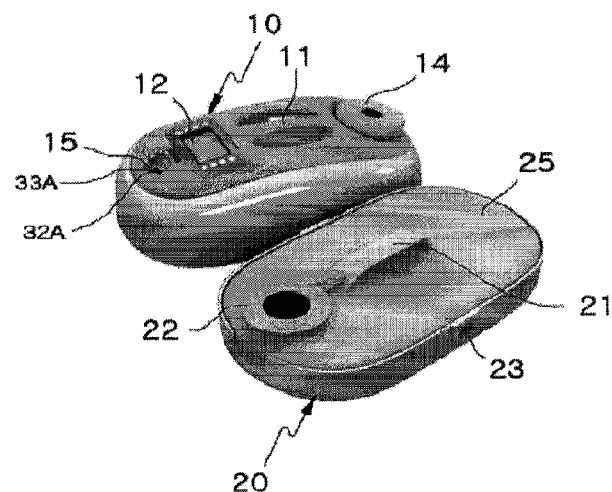
FIG. 2 is an exploded perspective views showing the state that the upper container and the lower container which are constructed the apparatus for analyzing body fluid of FIG. 1 are connected.

FIG. 1 is a perspective view of the quantitative analysis apparatus of a body fluid according to a preferred embodiment of the present invention. The quantitative analysis apparatus of a body fluid 100 is plugged into an adapter 40 (FIG. 3) on the tip of the quantitative analysis apparatus of a body fluid in the body fluid collector (FIG. 4) via a joint socket 15, so that the analysis apparatus 100 can measure the volume and constituents of a body fluid as a body fluid supplied through the body fluid collector passes through it. As depicted in FIG. 2, a housing constituting the analysis apparatus 100 is largely constituted by an upper case 10 and a lower case 20.

Figure 3:
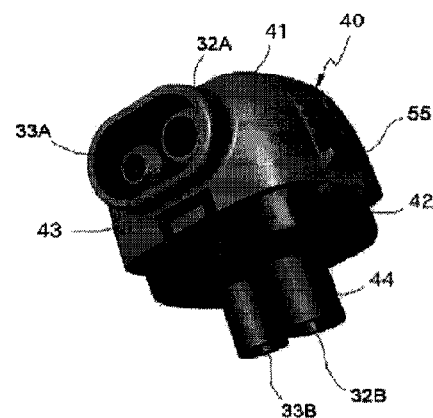
FIG. 3 is a perspective view of the adapter which is used in connecting the body fluid collecting part of the present invention to the apparatus for analyzing body fluid.

Referring to FIG. 3, the upper case 10 and the lower case 20 are designed to be detachable/attachable from/to each other in a vertical direction by a button 30 with an elastically mounted spring on one side of the central part of the outer surface of the lateral wall. Now that the upper case and the lower case of the analysis apparatus of the present invention are detachable from each other, the container 25 that is relatively more susceptible to contamination may be isolated separately from the other constituents and be hygienically treated to ensure safe use.

In addition, a handle 11 is formed on the upper end of the upper case 10, and a display and control unit 12 is installed in front of the handle 11 to make implement the quantitative analysis of a body fluid. In front of the display and control unit 12, the joint socket 15 is formed, into which an adapter 40 (in FIG. 3) of the body fluid collector is inserted.

Figure 47:
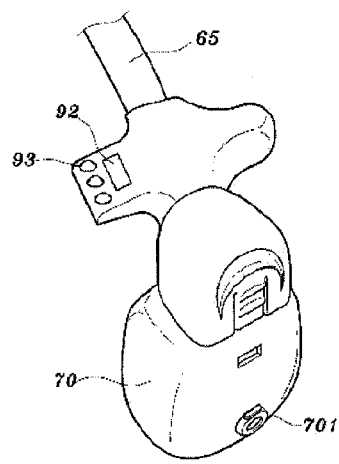
FIGS. 47, 48 and 49 show the aspect that the driving motor and the impellor or the fan is additionally installed in the collecting apparatus.
Figure 48:
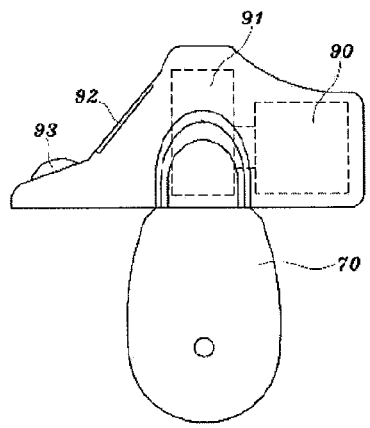
Figure 49:
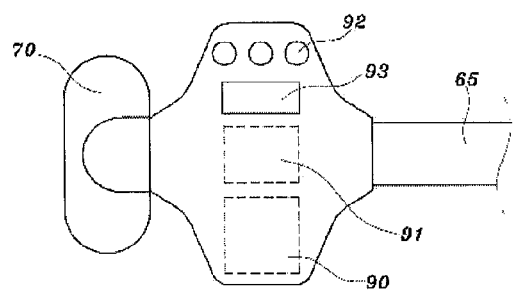

One of the joint socket 15 is a cable to connect to the power supply, through which the collector is connected to a sensor part 62, and it can be functioned as means for the power supply if a driving motor 90 and impellor 91 or pan is additionally equipped in the collector (FIGS. 47, 48 and 49).

The lower case 20 is equipped the body fluid container 25, and is installed the lower container handle 21, and ball and the body fluid container having the packing part 22 at the left side.

The lower case 20 and the container 25 are constructed to be separated and assembled via a screw 23 of the lower part.

As shown in FIG. 3, the body fluid (urine) passage 32a and the cleansing water passage 33a are established in the upper body 41 of the adapter respectively, and the body fluid (urine) passage 32b and the cleansing water passage 33b are established in the lower body 41 of the adapter respectively.

Figure 4:
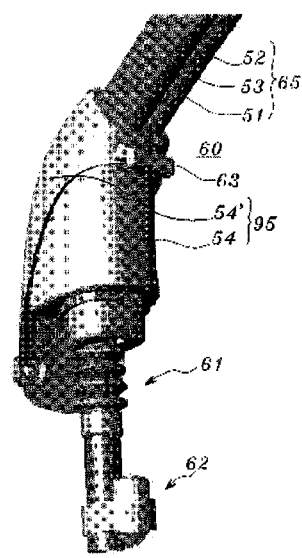
FIG. 4 is a perspective view showing one embodiment of the body fluid collecting part which is constructed the apparatus for collecting body fluid of the present invention.
Figure 7:
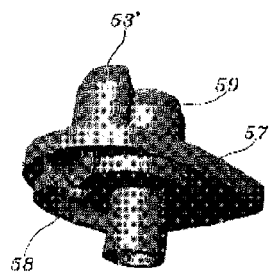
FIG. 7 is an enlarged perspective views showing the middle body which is constructed the body fluid collecting part of the present invention.

In addition, the cleansing water passage 33a of the adapter is connected to the washing tube 53 which is one of the total tube 65 of the body fluid collecting part of FIG. 4 and to connect to the connecting hole 53' of the middle body in the body fluid collecting part as shown in FIG. 7. The body fluid passage 32a of the adapter is connected to the body fluid tube 51 which is another one of the total tube 65 of the body fluid collecting part and to connect to the absorbing part 61 and the fixing tube 64 via 59 of FIG. 7.

The cleansing tube 53, the body fluid absorbing tube 51 and the sensor tube 52 are wrapped with the total tube 65 which did not shown, and the sensor tube 52 is connected to the separate cable in the connecting hole 15.

Figure 5:
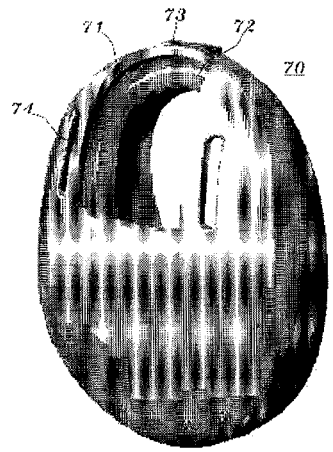
FIG. 5 is a perspective view showing one embodiment of the body fluid collecting part case for woman, which is constructed the apparatus for collecting body fluid of the present invention.
Figure 19:
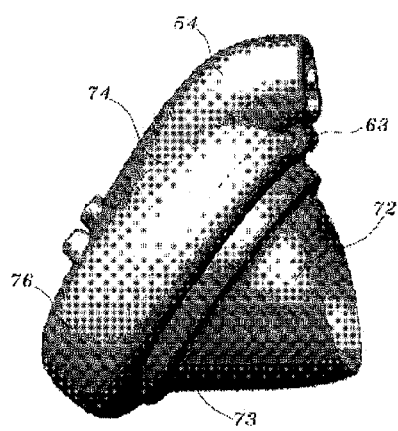
FIG. 19 is a perspective view showing one embodiment of the body fluid collecting case for man according to the present invention.

In the present invention, the apparatus for collecting body fluid 50 is used by combining the collecting part 60 of FIG. 4 and the collecting part case 70 for woman of FIG. 5 or the collecting part case 70' for man of FIG. 19.

FIG. 4 shows one embodiment of the apparatus for collecting body fluid according to the present invention, in which the body fluid collecting part consists of the collecting body 95, the adapter 40 and the total tube 65 connecting the collecting body and the adapter.

The collecting body 95 consists of the neck part 54' and the fixing body 54 of the collecting part. The neck part 54' and the fixing body 54 are a single structure, however in combining with the collecting part case, it is classified the structure protruding outside of the collecting part case with the neck part 54' and the structure inserting into inside of the collecting part case with the fixing body 54. Such classification can be concluded the construction of inner structure according to the combination method in combining the collecting part and the collecting part case. For embodiment, it can be possible to classify like FIG. 20 or FIG. 21 as describing later on.

Moreover, the structure to perform the different object can be attached to the neck part 54' and the fixing body 54. For embodiment, the dry fan capable of increasing the ventilation ability to prevent fester of skin and the gas sensor capable of automatically recognizing the excrements can be installed in the neck part 54' of the collecting part and the fixing body is constructed with the structure capable of bidet cleansing with the opening of the cleansing tube and the absorbing tube capable of fluid moving to the direction of gravity with its own weight, and the liquid recognizing sensor because the biosensor capable of measuring the specific constituent of the body fluid can be installed.

The gas sensor installing at the neck part 54' of the collecting part can be a diversity of sensors, however the ammonia gas sensor is most preferable as the evacuation sensor.

In addition, each passages forming the absorbing tube 51, the sensor tube 52 and the cleansing tube 53 are combined with a single body in the total tube.

In addition, since the body fluid absorbing part 61 and the sensor part 62 of the present invention has the structure of freely flowing in the collecting part cases 70 and 71' in the direction of gravity, it is always located in the lower part of the collecting part case 70 with moving the absorbing part 61 and the sensor part 62 according to the state of a posture in case of changing a posture for preventing bedsore as being worn by a patient by assembling the apparatus for collecting body fluid 50 (FIG. 8) and it can perform the function of recognizing and absorbing liquid pooled in the direction of gravity since the liquid recognizing sensor located below immediately recognizes the urine as urinating in such state and it take absorbing behavior through the absorbing part.

A sensor of the sensor part 62 can be constructed with an optical sensor, an electrode sensor, a thermal sensor, an air pressure sensor and a float sensor.

As shown in FIG. 5 as one preferred embodiment of the present invention, in the collecting part case 70 combined with the body fluid collecting part 60, the fixing body 54 of the body fluid collecting body 60 is inserted with installing into a sphere or cylindrical case, the stumbling projection 73 is formed in the upper part and the air hole 74 is formed in the center part of the collecting part case or the right and left side of the inserting hole 71 as necessary.

The contact part 72 is attached to the inner side of the collecting part case and it attach around the openings to maintain the airtight with the perineal region of the human body, and the contact part 72 is formed by soft silicone material, and the total tube 65 can be formed any material which is used in a disposable liquid supplying line, for embodiment rubber, silicone or forming silicone material, and forming silicone is most preferable among them.

In the present invention constructed as such, the contact part 72 of the collecting part case 70 is formed by soft silicone material in case that the object of collecting is the urine and is contacted to the perineal region of the human body such that liquid (urine or cleansing water) is flowed into the apparatus for collecting body fluid without leaking and is recognized by the sensor part 62 and is absorbed in the absorbing part 61 by the driving motor and is introduced to the quantitative analysis apparatus for body fluid and the quantitative analysis is performed at the same time with the urination.

Figure 6:
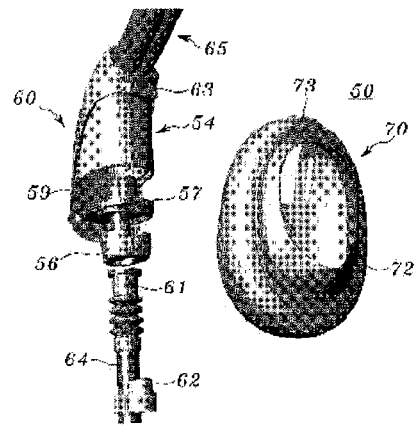
FIG. 6 is a whole exploded perspective views showing one embodiment of the apparatus for collecting body fluid of the present invention.

Since the present invention is characterized in that the total tube 65 connecting to the neck part of the body fluid collecting part is installed at the upper side or back side of the collecting part case 70 and the total tube is located in the upper side of the collecting part case, when a patient wear with combining the apparatus for collecting body fluid as shown in FIG. 6, it can be possible to prevent the phenomenon of being pressed the total tube by the human body such as the perineal region as a patient is seated on a seat such as wheel chair, and to solve the problem of being closed the total tube by bending. Accordingly, the apparatus for collecting body of the present invention can be worn in the sit-down posture and thus it can be use usefully while user is out.

FIG. 6 shows a preferred one embodiment of the body fluid collecting part 60 and the collecting part case 70 in the apparatus for collecting body fluid of the present invention, especially shows a deal perspective view of each components combining to the fixing body 54 of the body fluid collecting part 60.

The middle body 57 forming the body fluid absorbing tube 59 and the cleansing tube 53 is fixed with fitting to the lower part of the fixing body 54 of the body fluid collecting part 60 and the lower body 56 is fixed with fitting to the lower part of the middle body 57.

In here, the hole 58 (FIG. 7) formed in the middle body 57 is a hole that the cable connecting to the sensor part 62 which is formed below it, is passed through.

The absorbing part 61 is fixed with fitting to the inserting hole of the lower part of the lower body 56 and the fixing tube 64 is fixed with inserting to the lower part of the absorbing part 61, and the sensor part 62 is fixed with inserting to other side of the fixing tube 64 and thus the body fluid collecting part 60 is formed as shown in FIG. 4.

In here, it has the structure that the upper part of absorbing part 61 is formed in the collapsible type and the fixing tube 64 which is played a role of a balance weight toward the direction of gravity is formed in the lower part and the upper part of the absorbing part 61 is fixed with fitting to the fixing body 54, however it can be possible the structure that the upper part of absorbing part 61 is formed in the collapsible type and the absorbing part itself play a role of a balance weight toward the direction of gravity, and the upper part of the absorbing part 61 is fixed with fitting to the fixing body 54.

The body fluid collecting part 60 having such construction is combined with the collecting part case 70 to complete the apparatus for collecting body fluid, in which the stumbling sill 63 formed in the upper side of the collecting part of FIG. 4 and the stumbling projection 73 of the collecting part case 70 of FIG. 5 are combined to fix.

Figure 8:
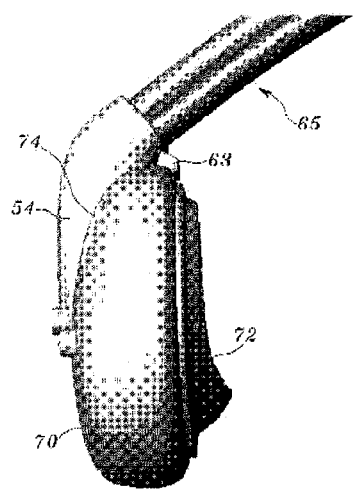
FIG. 8 is a whole combined perspective views showing the state that the apparatus for collecting body fluid of the present invention is combined.

Namely, the stumbling sill 73 is fixed with fitting to the stumbling projection with inserting the body fluid collecting part 60 into the inserting hole 71 as showed in FIG. 8. Meanwhile, in separating them, the stumbling sill 73 is separated from the stumbling projection 63 by pushing the fixed body 54 of FIG. 4 in the state of combining and rotating the inserting hole 71 of the collecting part case 70 with pushing, and then the body fluid collecting part 60 and the collecting part case 70 are easily separated such that it can be used sanitarily by exchanging and washing the case only.

Namely, there is provided the structure that the lower part of the opening of the collecting part case 70 is contacted to the perineal region of the human body away off the anal and it is not contaminated by the excrements, however even if it were so, since only the collecting part case 70 is contaminated and the locking device of the fixed body of the body fluid collecting part and the locking device of the collecting part case are capable of assembling and separating each other, it can be used sanitarily by exchanging and washing the case only.

In addition, it is preferred to a patient in the aspect of wearing feeling that the total tube 65 is constructed to wind from the collecting part cases 70 and 70' toward the pelvis of the human body and the most wearing feeling is obtained in case of 120.

In here, the locking device consists of the stumbling sill 63 of the fixed body and the stumbling projection 73 of the case 70, however it is not limited to them.

Figure 9:
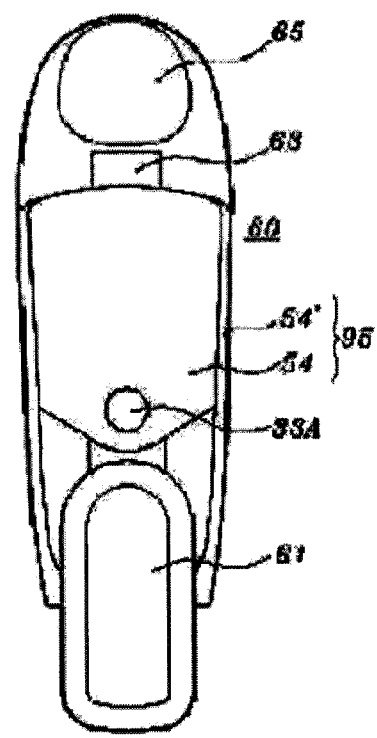
FIG. 9 is a front view showing another embodiment that the flowing body is combined to the apparatus for collecting body fluid of the present invention.

Meanwhile, FIG. 9 is a front view showing another embodiment in which the collecting part and the flowing body of the apparatus for collecting body fluid of the present invention are combined.

In the apparatus for collecting body fluid, the total tube 65 is pass through, and the neck part 54' of the collecting part combined to the total tube 65 has the stumbling sill 63 in the upper portion or both right and left side portion and thus the collecting part case 70 is fixed with fitting to the stumbling sill 63.

The collecting part 60 as described in the first embodiment has three passages such as the body fluid passage, the cleansing water passage and the cable passage.

The cleansing water passage 33a is formed in the shape of project from inside of the collecting part 60 to outside, the flowing body 61 with the built-in absorbing part and sensor part in the structure of joint type is fixed in the fixing body 54 of the collecting body, and such flowing part is constructed to locate in the direction of gravity based on joint of the flowing part 61 with its own weight.

The flowing part as referring to the following has the sensor part 62 and the flowing body passage 104 formed therein.

In the former embodiment, the absorbing part is formed in the flowing part to the downwards however the absorbing part of this embodiment is formed in the flowing part to the direction of joint. On this wise, the direction of the absorbing part is established to the backward of the flowing part, namely toward the collecting part case side such that the function of absorbance can be completely embodied even the patient use it in sit-down posture. The absorbing part can be formed in the forward or the backward of the flowing part according to a use.

Figure 10:
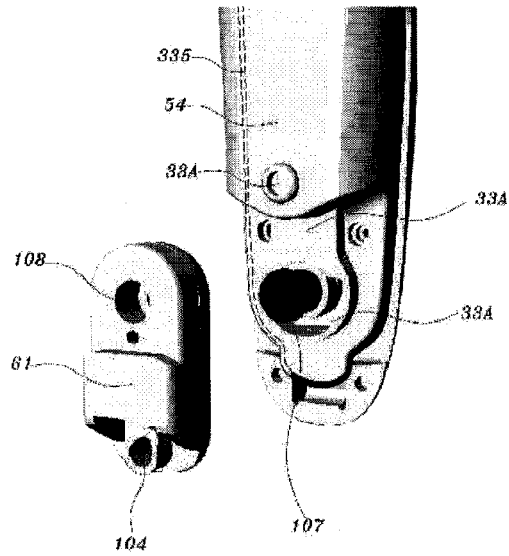
FIG. 10 is an exploded view showing the structure that the flowing body of the present invention can be fixed on the body of the body fluid collecting part.

FIG. 10 a disassembled perspective view showing the structure capable of fixing the flowing body 61 to the collecting part fixing body 54. O ring 335 of silicone or rubber material is inserted in the outside part of the collecting part fixing body 54 to fix with assembling to the collecting body 95.

In the outside, the middle connecting body 110 for connecting the collecting part fixing body and the flowing body 61 is fixed in the lower part of the collecting part fixing body 54 forming the cleansing water passage 33a.

The middle connecting body 110 is fixed with fitting to the body fluid passage and the cleansing water passage 33a in the collecting part fixing body 54 as described above, and has the structure capable of locking the flowing body 61 as to the following.

In addition, the total tube 65 is preferred that of getting bent toward the pelvis of human body in the collecting part cases 70 and 70' because of its wearing feeling for the patient, and most preferred is that of getting bet with 120 degrees.

Figure 11:
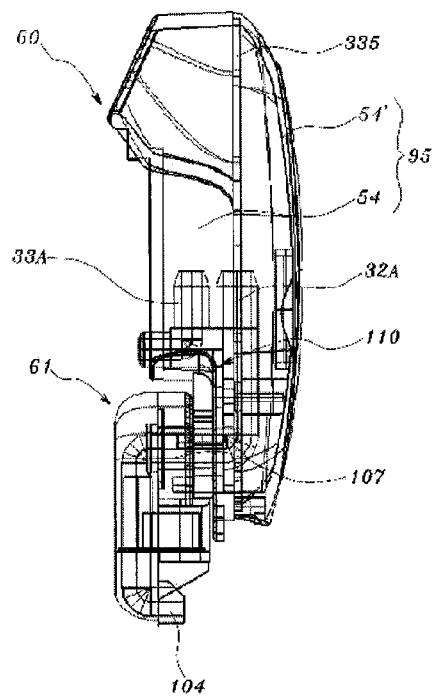
FIG. 11 shows a cross-section view of the one side of the body fluid collecting part of the present invention.

As shown in FIG. 11, in the center of the middle collecting body 110, the connecting pole 107 for fixing is fixed in the passage connected with the body fluid passage, and the end of the connecting pole 110 is formed in the type of 고 to prevent separating in locking via the inserting groove 108 of the flowing body 61.

The flowing body 61 has the inserting hole 108 in the upper part for connecting to the connecting pole 107 and has the sensor for sensing the body fluid in the inner part and has the flowing body passage 104 in the lower part, and a half arc type large long hole 109 is formed around the connecting pole 107 in order to insert the cable induced from the sensor therein such that it can prevent the phenomenon that as the flowing body 61 is located in the direction of gravity with its own weight, it is caught by the cable.

Figure 12:
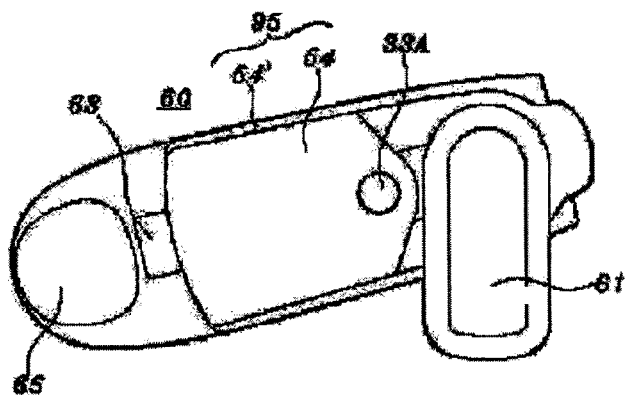
FIG. 12 is a perspective view showing the state that the body fluid collecting part of the present invention is located to the direction of gravity with its own weight.

The connection relationship of such construction can be understood by FIG. 12.

Figure 38:
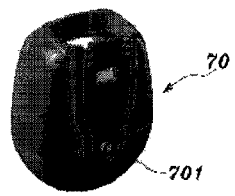
FIG. 38 is a back perspective view of the collecting part case of the apparatus for collection body fluid according to the present invention.
Figure 39:
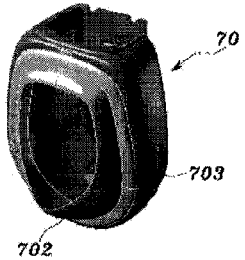
FIG. 39 is a perspective view showing that the body fluid collecting part and its case of the apparatus for collection body fluid according to the present invention are separately displayed.
Figure 40:
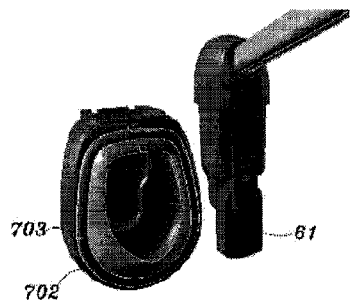
FIG. 40 is a perspective view showing that the body fluid collecting part and its case of the apparatus for collection body fluid according to the present invention are separately combined.
Figure 41:
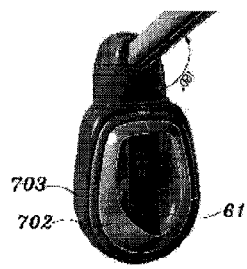
FIG. 41 shows the body fluid collecting part and its case as a single unit.
Figure 42:
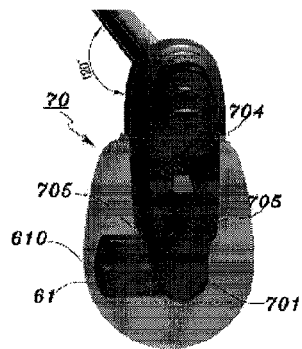
FIGS. 42, 43 and 44 are perspective views showing that the electrode sensor is installed in the body fluid collecting part of the apparatus for collection of body fluid according to the present invention.

The body fluid collecting part having such construction, as detailed shown in FIGS. 38 and 39, can be used by assembling in the collecting part case 70, in which the perineal region attaching part 702 and the case 70 are contact with the Teflon material 703 and are locked by the body fluid collecting part 60 having the flowing body therein and the elastic barb 704 (FIGS. 40, 41 and 42.)

The collecting body 95 consists of the collecting part body 54 and the neck part 54' with a single body, and the middle connecting body 110 is combined in the inner side of the collecting part body 54.

The inserting groove 108 of the flowing part 61 is connected to the middle connecting body 110 having the cleansing water passage 33a and the body fluid passage 32a via the "工" type connecting pole 107 to fix to make freely moving.

It is preferred that the flowing part 61 and the absorbing part is made by Teflon material which has good contacting ability and is rarely worn down.

That is to say, FIG. 12 a perspective view showing that the flowing part 61 of the body fluid collecting part 60 is located to the direction of gravity or to the right or left direction in 180 degrees with its own weight.

As described above embodiment 1, when the urine is sensed by the body fluid sensor, it absorbed in the absorbing passage and after absorbing completed, the cleansing water is spouted from the cleansing water passage to be acted like a bidet and then the cleansing water is absorbed in the absorbing passage.

The characterization of the present invention is that it can be possible to accurately detect the body fluid at all times since the sensor is located to the direction of gravity though the body fluid in the case is flowed together with carrying out the basic operation.

The sensor can be constructed with a sensor capable of recognizing for the body fluid, such as an optical sensor, an electrode sensor, a thermal sensor, an air pressure sensor or a float sensor, and a signal from the sensor part can be wireless transmitted (or received) to (or from) the quantitative analysis apparatus for body fluid.

Figure 13:
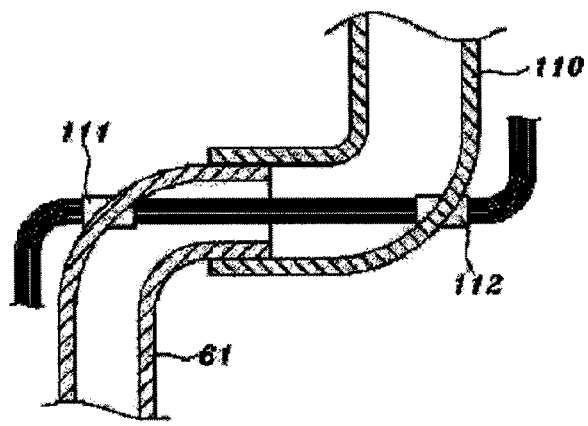
FIG. 13 is a partial cross-section view showing another embodiment of the joint structure according to the present invention.

FIG. 13 is a perspective view showing a joint structure according to another embodiment of the present invention.

In here, it will be omitted the figure and sign to the similar part as described above and be explained to the part having different constructions.

The middle connecting body 110 and the flowing part 61 are tightly fixed with inserting and assembling each other and the cable combining holes 111 and 112 are formed in the right and left end of the hollow axis 113 which penetrates almost in the middle of the middle connecting body 110 and the flowing part 61 at center such that the cable 114 pass through the cable combining holes 111 and 112 to connect to the sensor.

In addition, the sensor is installed at side part of the fluids passing tunnel 104 of the flowing part 61 and then the cable 114 being connected to the sensor is drown out.

The cable combining holes 111 and 112 has bolt type structure to endow water proof ability to the fluid, and in some cases they are allowable to be constructed in one cable connecting pipe.

In such joint type connecting device, when the flowing part 61 fixed in the middle connecting body 110 is located in the direction of gravity with its own weight, although the flowing part 61 is rotating 180 degree according to the gravity in the middle connecting body 110, there is an effect on rotating more easily with the resistance of the cable since it rotates with the both cable connecting holes 111 and 112 as the central figure and the inner cable is not get tangled.

Figure 14:
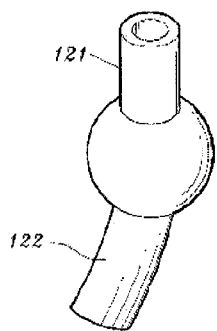
FIG. 14 is a partial perspective view showing another embodiment of the joint structure according to the present invention.
Figure 15:
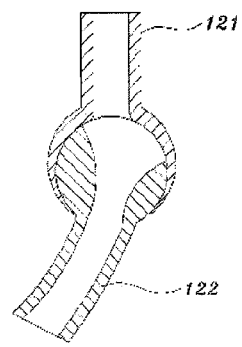
FIG. 15 is a partial cross-section view showing another embodiment of the joint structure according to the present invention.

FIGS. 14 and 15 are a perspective view and a partial section view showing a joint structure according to another embodiment of the present invention.

In here, it will be omitted the figure and sign to the similar part as described above and be explained to the part having different constructions.

That is to say, it can be possible to construct the middle connecting part that it, as shown by the figure, is formed as the upper joint 121 in the shape of sphere, and the lower joint 122 is inserted in the upper joint 121 as the flowing body and thus it maintains the airtight and makes flowing each other.

Such joint structure also has an effect that it can be easily rotated when the sensor is installed in the lower joint and the lower joint which is the flowing body is located in the direction of gravity at the centroid.

Figure 16:
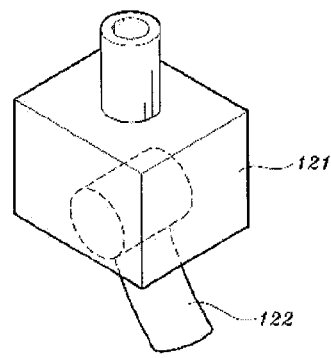
FIG. 16 is a partial perspective view showing another embodiment of the joint structure according to the present invention.
Figure 17:
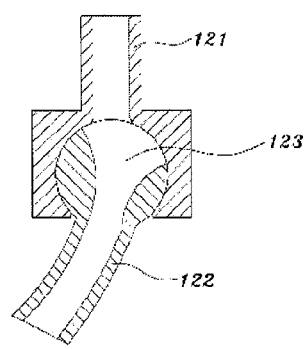
FIG. 17 is a partial cross-section view showing another embodiment of the joint structure according to the present invention.

FIGS. 16 and 17 are a perspective view and a partial section view showing a joint structure according to another embodiment of the present invention, in which a basic construction is similar to that of FIG. 14 but it is different in that the joint is not a sphere type but a cylindrical type.

Figure 18:
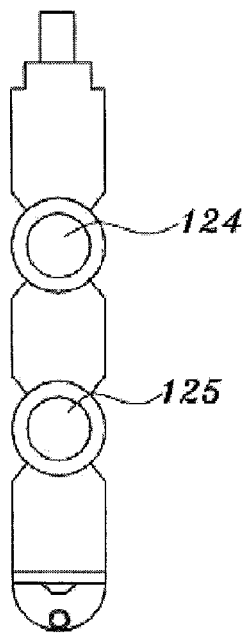
FIG. 18 is a partial cross-section view showing another embodiment of the joint structure according to the present invention.

FIG. 18 is a partial section view showing a joint structure according to another embodiment of the present invention, which shows multi joint structure.

In such an embodiment, the $1_{st}$ joint 124 and the $2_{nd}$ joint 125 are connected to the middle connecting body 110 one after another, and the $2_{nd}$ joint 125 has the flowing structure described above and the $1_{st}$ joint 124 can be formed a tunnel for cleansing water therein.

Meanwhile, the collecting part case 70 for woman of the present invention has a construction that the contact part 72 made by soft silicone material is tightly contact to the perineal region. The collecting part case 70 for man shows in FIG. 19.

The collecting part case for man has the same construction with the case for woman except that the lower part of the contact part 72 attached around the inserting hole 71 is extended to cover the glans of the penis and an angle in using is different.

Figure 20:
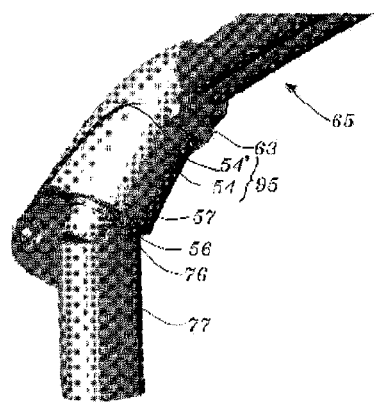
FIG. 20 is another exemplification view of the body fluid collecting part according to the present invention.

FIG. 20 different from FIG. 4 is a perspective view showing another embodiment of the body fluid collecting part according to the present invention.

The lower body 56 is combined with the fixed body via the middle body 57 and has joint holes at the front and the rear, and the flowing tube 77 is formed in order to make a construction of joints type in which the joint bundle 76 combined to the joint hole is connected.

The flowing tube 77 has the absorbing part and the sensor part formed therein and is always toward to the direction of gravity by it own weight.

By using the flowing tube with joints, it has an effect to solve the vibration problem which can be occurred by the tremor phenomenon in absorbing liquid at the single tube structure or the structure consisting of only a collapsible tube since it winding to the right and left side in carrying out the function of recognizing and absorbing liquid pooled in the direction of gravity.

Figure 21:
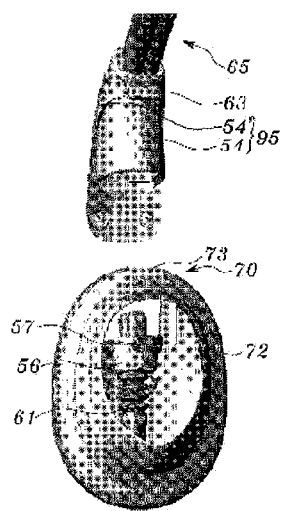
FIG. 21 is another exemplification view of the body fluid collecting part according to the present invention.

FIG. 21 shows another embodiment of the apparatus for collecting body fluid according to the present invention, in which the collecting part and the collecting part case are attachable and detachable.

In this figure, another embodiment to the attachable and detachable collecting part case is provided in which the collecting body being connected the total tube 65 is divided into the neck part 54' and the fixed body 54, and the fixed body 54 combined the absorbing part and the sensor part are combined is fixed in inner side of the case 70 to make the attachable and detachable construction of the collecting body and the collecting part case.

Also at this time, the stumbling projection 73 of the case 70 is constructed to be attachable and detachable to the stumbling sill 63 of the upper side of the fixed body 54

Figure 22:
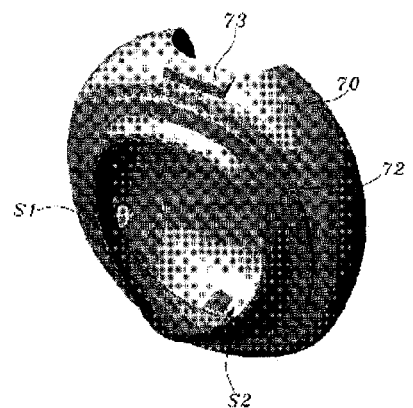
FIG. 22 is an exemplification view showing the state that the sensor is installed in the body fluid collecting part case according to the present invention.

FIG. 22 shows another embodiment of the collecting part case 70 of the present invention, in which many of separate sensor (S1), (S2) are constructed in the case 70.

In this case, the urine absorbing part is not necessary to constructed with the sensor part. That is, only the absorbing part can be separately constructed from the sensor part to freely bend to the direction of gravity since three sensors are installed on the lower part and the both side part of the case such that although the case 70 is rotating and thus the body fluid in the case is flowing together, the sensor can detect the body fluid.

Figure 43:
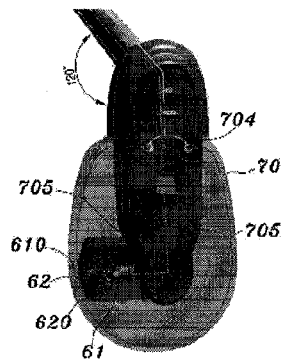
Figure 44:
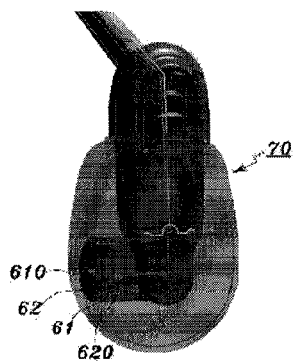

The sensors S1 and S2 can be constructed with a sensor capable of recognizing for the body fluid, such as an optical sensor, an electrode sensor, a thermal sensor, an air pressure sensor or a float sensor (FIG. 29), and a signal from the sensor part can be wireless transmitted (or received) to (or from) the quantitative analysis apparatus for body fluid. A float sensor is a weight direction recognizing sensor, in which a large number of absorbing hole for collecting the urine 622 are equipped on the inner side of the collecting part case and the absorbing hole is opened and closed by electronic method, for embodiment by a solenoid valve 623. Moreover, in practicing the present invention, preferred type of the electrode sensor is shown in FIGS. 43 and 44.

Figure 30:
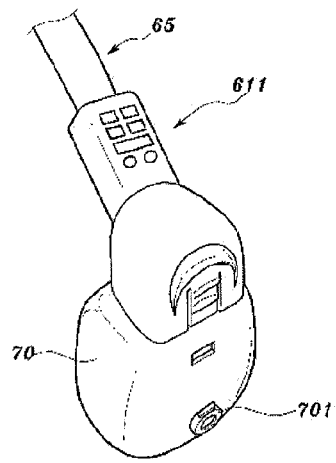
FIG. 30 is a perspective view showing another embodiment of the body fluid collecting part according to the present invention in which the control panel is installed on the upper part of the body fluid collecting part according to the present invention.
Figure 31:
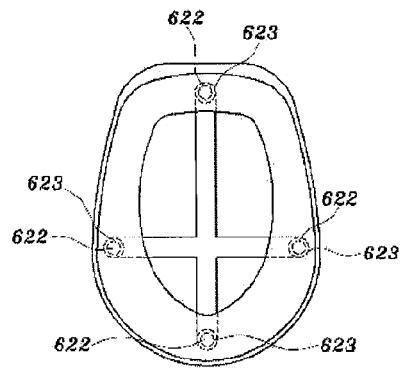
FIG. 31 is a front view of the collecting part installing the gravity direction recognizing sensor in which a large number of absorbing hole for collecting the urine is formed in the inside external of the body fluid collecting part case according to the present invention and the open and close can be controlled by the solenoid valve.
Figure 32:
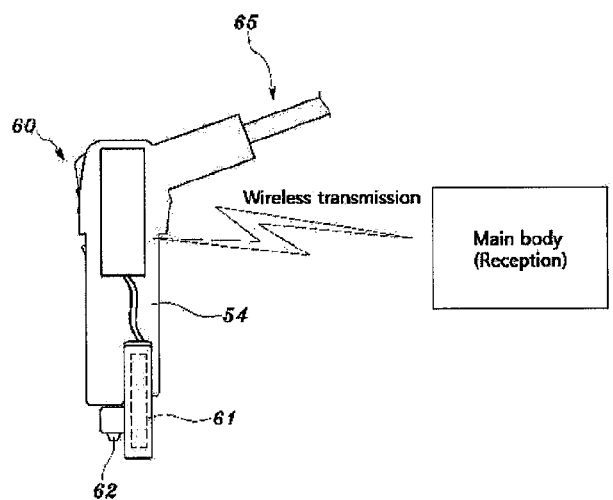
FIG. 32 is an exemplification view showing that a preferred signal transmitting wireless system is introduced in the sensor part of the analysis apparatus for body fluid according to the present invention.
Figure 36:
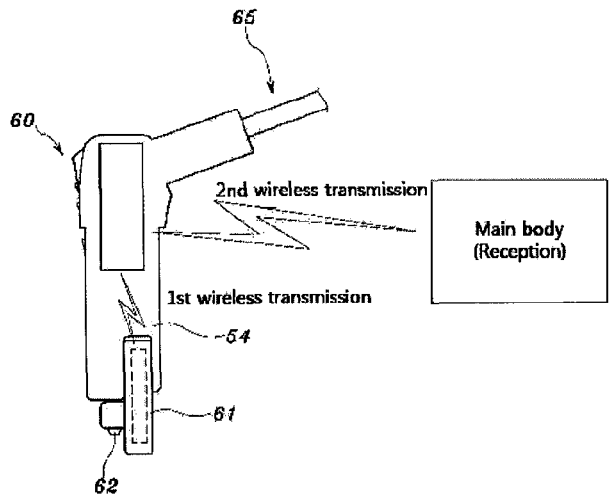
FIG. 36 is an exemplification view showing that the signal transmitting wireless system is introduced to the sensor part of the analysis apparatus for body fluid according to the present invention.
Figure 37:
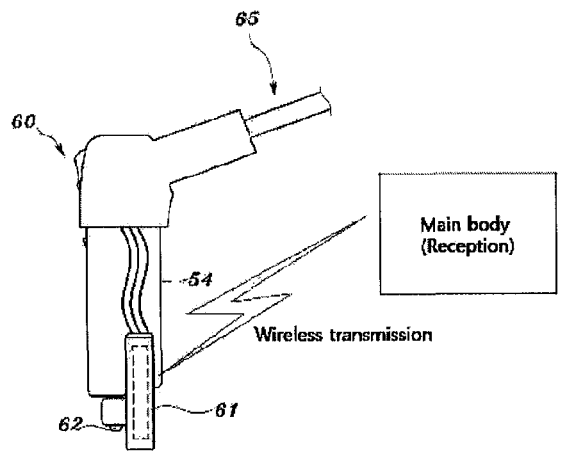
FIG. 37 is another exemplification view showing that the signal transmitting wireless system is introduced to the sensor part of the analysis apparatus for body fluid according to the present invention.

Preferably, a float in FIG. 32 and FIG. 36 has a reception box and the $1_{st}$ wireless transmission and the $2_{nd}$ wireless transmission can be carried out by the $1_{st}$ wire transmission and the $2_{nd}$ wire transmission as shown in FIG. 37. It has RFID transmitting/receiving part in the sensor part and the main body of the body fluid collecting part respectively. (FIG. 30)

RFID (Radio Frequency Identification) is a technique for providing a foundation capable of recognizing, tracing and controlling objects by using a wireless radio frequency.

It can be constructed with a system that a power supply is not necessary in the receiving part as electric power is emitted by a radio wave.

A permissible frequency of RFID is blow 135 KHz (for stock farming), 13.56 KHz (for a library), 433.92 MHx (for container, 100 m), UHF (860 MHz-960 MHz, for physical distribution), 2.45 GHz (for a passport, RFID).

In the present invention, with a distance of the sensor part and the main body being up to 10 m, UHF frequency is used. UHF frequency is harmless to the human body because it same with TV frequency.

In the present invention, an RFID transmitting/receiving part of the main body provides an electric power by using the relevant frequency and an RFID transmitting/receiving part of the sensor part accumulating an electric power and become an active state.

When the RFID transmitting/receiving part of the main body transmits a command after proving the relevant ID to the RFID transmitting/receiving part of the sensor part, the RFID receiving part of the sensor part receives the relevant ID and perform the urine measuring and inform the result to the RFID transmitting/receiving part of the main body.

The protocol is as follows:

An urine measuring order (the main body→the collecting part): a receiving ID (1 Byte)—an urine measuring order code (1 Byte) CRC (1 Byte)

An urine measuring or not (the collecting part→the main body): a receiving ID (1 Byte)—an urine measuring result (1 Byte) CRC (1 Byte)

Figure 33:
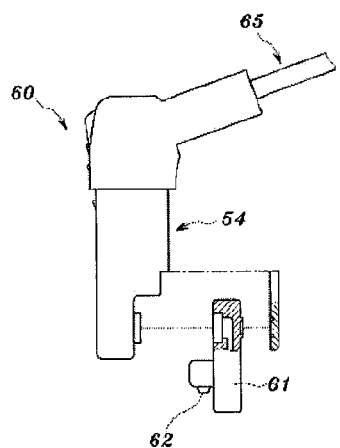
FIG. 33 is an exploded perspective view showing the state that the sensor part and the flowing body are combined to the fixing body of the analysis apparatus for body fluid according to the present invention.
Figure 34:
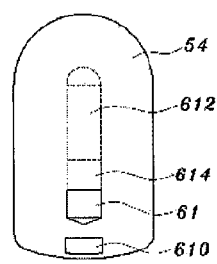
FIG. 34 is a front view showing the structure of a battery-powered sensor part and the flowing body of the analysis apparatus for body fluid according to the present invention.
Figure 35:
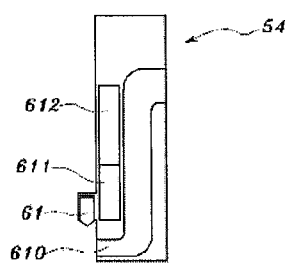
FIG. 35 is a cross-section view showing the structure of a battery-powered sensor part and the flowing body of the analysis apparatus for body fluid according to the present invention.

Another embodiment is that a urine measuring sensor of the sensor part is connected to the collecting part by a cable and a RF transmitting part having 400 Mhz/900 Mhz/2.4 Ghz ISM band field is installed in the collecting part and the collecting part is driven with a separate power supply (FIGS. 33 and 34).

In the main body, a RF transmitting part having the same frequency band with the collecting part is installed.

A frequency of ISM band has following protocols because a radio wave is in danger of collision.

An urine measuring order (the main body→the collecting part): Sync data (2 Bytes)—a receiving ID (1 Byte)—an urine measuring order code (1 Byte) CRC (1 Byte)

An urine measuring or not (the collecting part→the main body): Sync data (2 Bytes)—a receiving ID (1 Byte)—an urine measuring result (1 Byte) CRC (1 Byte)

Figure 23:
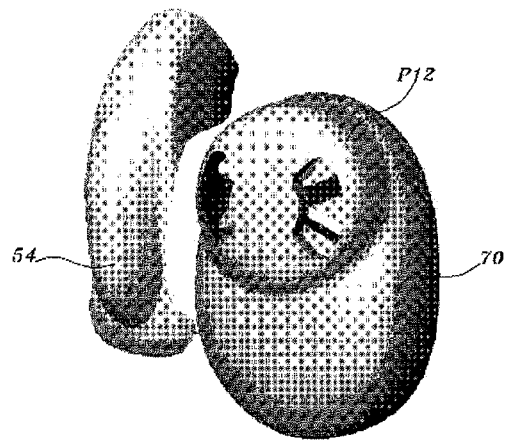
FIG. 23 is an exemplification view showing the state that the ventilation hole is formed in the body fluid collecting part case according to the present invention.
Figure 24:
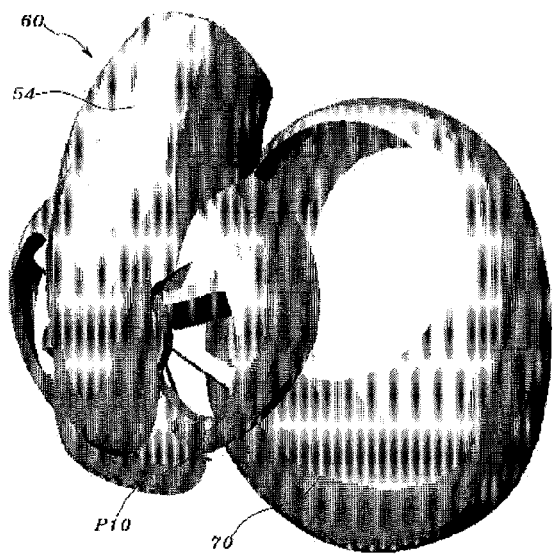
FIG. 24 is an exemplification view showing the state that the fan installing part is formed in the body fluid collecting part according to the present invention.
Figure 25:
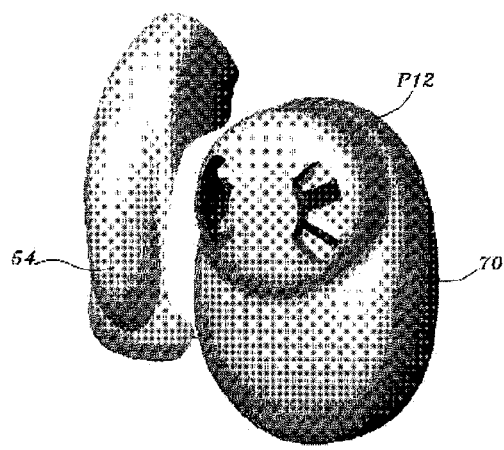
FIG. 25 is an exemplification view showing the state that the fan installing part is formed in the body fluid collecting part case according to the present invention.

Meanwhile, FIGS. 23 to 25 show another embodiments of the collecting part case according to the present invention, which are mainly show a ventilating construction of the collecting part case.

FIG. 23 shows a number of ventilating hole P12 having a structure of the rib of a fan for ventilating the collecting part case 70 connected with the body fluid collecting part 60.

By such a ventilating hole P12, it can be possible to prevent fester of a skin by increasing airing in wearing for a long time.

Moreover, it can be obtained ventilating effects by covering the body fluid collecting part case 70 with a disposable consumption cotton fabric in which a large number of minuteness ventilating holes are formed.

FIG. 24 shows a fan installing hole P10 for installing a motor and an impellor to the body fluid collecting part 60, in which an operating mechanism that the collecting part and the collecting part case 70 are attached and detached is same as described above. As another embodiment 611 in which a driving motor 90, the impellor 91 and an LCD panel 92 are equipped and a controlling button 93 is installed, is showed in FIG. 28 or FIGS. 47 and 48.

FIG. 25 shows a fan installing hole P12 for installing a motor and an impellor in the collecting part 70.

FIGS. 24 and 25 can provide more comfortable environment even wearing for a long time than the case of compulsory ventilation by fixing a fan installed a motor to the fan installing holes P10 and P12.

Figure 28:
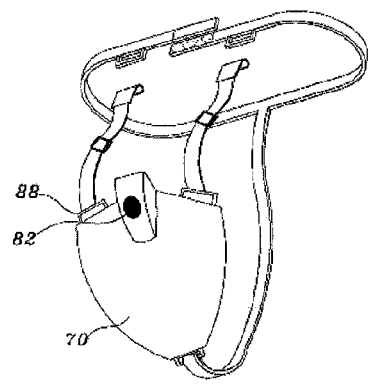
FIG. 28 is a perspective view showing another embodiment of the collecting case in using the apparatus for collection body fluid together with a diaper exclusive for a patient.

Moreover, the collecting part of the body fluid collecting part, and a driving motor and an impellor as a construction element for a drying fan in the collecting part case (70) can be installed respectively one from another, and the same result can obtain by installing the fan in the collecting part and the motor in the case (FIG. 28). On the contrary, the same result can obtain by installing the impellor fan in the collecting part case and the motor in the collecting part.

FIGS. 26 to 29 show another preferred embodiment of the present invention, in which the apparatus for collecting body fluid 50 has a structure which can be possible to be wearing together with the diaper exclusive for a patient 87.

Figure 26:
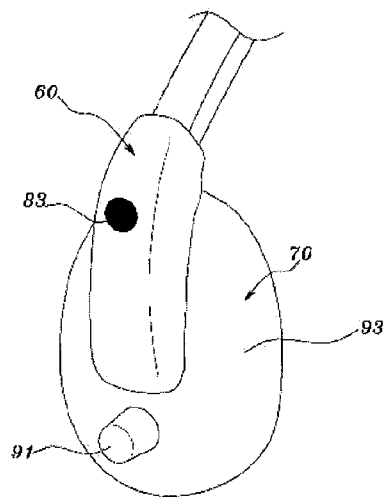
FIG. 26 is a perspective view showing the construction of the collecting part case in using the apparatus for collection body fluid together with a diaper exclusive for a patient.

FIG. 26 shows a collecting case 70 combine with the body fluid collecting part (60), in which a magnet fixing part is formed as one body in the cervical region of the collecting part.

The fixed locking supporting device (FIG. 27) can be constructed with a fixed rack, a fixed connection belt and a stomach band. The fixed rack 91 has a magnet therein in which magnetism is functioned correspond to a magnet fixing rack formed in the neck of the collecting part. The fixed connection belt connected to the fixed locking supporting device can be formed in three or four directions. In case of three directions, it has a spoke like in T type panties, and in case of three directions, it has a spoke like in general panties such that it can be easily locked to the stomach band. One aspect accomplished such object is that a hook is formed on end of the fixed connection belt and a ring capable of locking a hook is formed on the stomach band.

Figure 27:
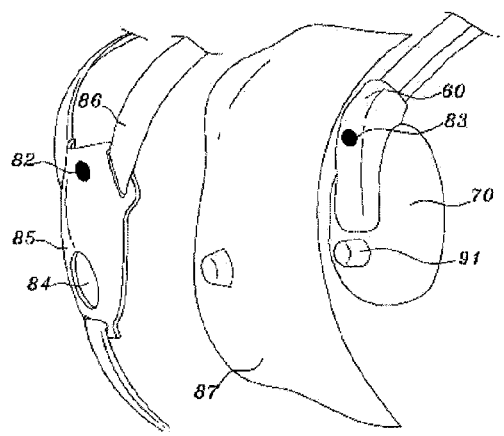
FIG. 27 is a perspective view of an embodiment that the apparatus for collection body fluid is used together with a diaper exclusive for a patient by using the locking supporting device.

FIG. 27 is a perspective view showing a locking state of the collecting apparatus 50 with the fixed locking supporting device 85 as shown to the diaper 87.

The fixed locking supporting device 85 has a connection device in which a fixed connection belt 86 is fixed in three (or four) directions and is injection molded with a magnet fixing device having a magnet 82 centrally inserted therein. Moreover, it can be possible to be formed the fixed locking supporting device, a magnet and a fixed connection belt together with a soft material such as rubber or silicone.

There is an effect that the apparatus for collecting body fluid of the present invention can be used together with the diaper 87 by using the fixed connection supporting device outside of a diaper since magnet 83 of the collecting apparatus together with a magnetic part 82 of the fixed connection supporting device 85 generate magnetism to fix on a fixed location for the diaper when the diaper 87 is located between the fixed connection supporting device 85 and the collecting part case 70 and the fixed connection belts 86 of the fixed connection supporting device 85 are fixed on body from three (or four) directions.

When the collecting apparatus is exactly located and fixed to the perineal region by using a connection supporting device outside of a diaper, there are advantages as follows:

First of all, an wear-fleeing is improving because the collecting apparatus can be adhered closely to the perineal region with appropriate pressure outside of a diaper.

Secondly, it can be surely coped with the situation of the evacuation because contamination with excrements in the evacuation can be minimized. That is, it is very convenient to hygienic manage because the fixed connection device is not contaminated as being located outside of a diaper, and only a disposable diaper which is contaminated with excrements is disused and the collecting part of the collecting apparatus is replaced and washed.

FIG. 28 shows a construction of a connection groove 88 capable of connecting fixed connection bands in the three or four directions around the collecting part case 70. Such connection device can be connected together with a diaper and it can be constructed like the fixed connection band of the fixed connection supporting device.

Figure 29:
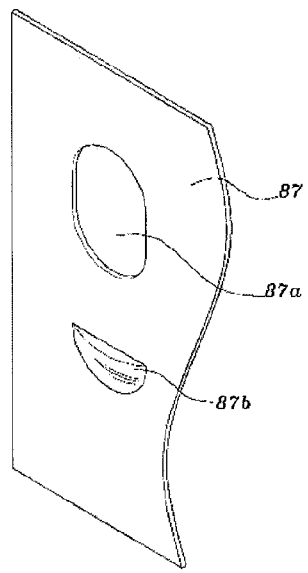
FIG. 29 is a perspective view of a diaper exclusive for a patient using in the apparatus for collection body fluid of the present invention.

FIG. 29 shows an exclusive diaper for the apparatus for collecting body fluid of the present invention, in which the exclusive diaper can be used together with the body fluid collecting part and a passing hole 87a of the collecting part is formed upper side of the diaper 87 and a membrane for preventing contamination with excrements 87b is formed under the passing hole 87a.

Accordingly, in using such diaper exclusive for patient, it can be possible to detach/attach the apparatus for collecting body fluid from/to the perineal region in state of wearing diaper and to increase ventilation effect and to more improve the wearing-feeling because hole is punched on the perineal region in which the part for collecting body fluid. In addition, it is characterized in preventing the collecting part case from the contamination with excrements in evacuation because the membrane for preventing contamination with excrements is installed under the hole.

Figure 45:
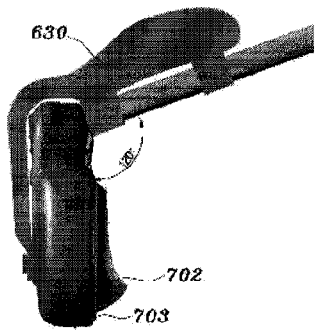
FIG. 45 is a perspective view showing the handle of elastic plastic material capable of fixing with easily attachable/detachable to the body fluid collecting part for woman in order to contact the collecting part case to the woman patient.
Figure 46:
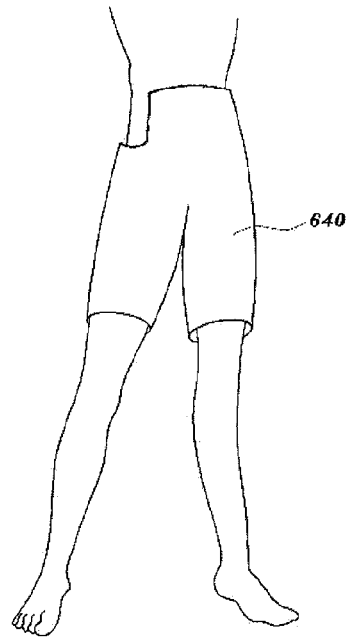
FIG. 46 is a perspective view showing that a diaper exclusive for woman patient capable of hiding the perineal region without having hip parts is wearing instead of a diaper exclusive for woman patient.

In order to exactly contact the collecting part case on the perineal region of woman, it can be possible to use elastic plastic handle 650 capable of fixing easily detachable/attachable on the part for collecting body fluid for woman (FIG. 45) and if possible, a diaper exclusive for a patient capable of covering only the perineal region without the seat 640 can be provided instead of a diaper exclusive for patient (FIG. 29) (FIG. 46)

In the meantime, the apparatus for collecting body fluid automatically treats the urination because of using the gas sensor as sensor part built in the collecting apparatus to reduce the number of times of diaper change such that it can be largely reduced manpower and a diaper usage necessary for the nursing. However, as a disposable diaper still used in evacuation, a sensor capable of automatically recognizing evacuation or not can be installed outside of a diaper to notice evacuation to a nurse with an alarm or a melody such that it can be possible to change a disposable diaper by clearly recognizing evacuation in the state of being weared a disposable diaper.

In order to embody the above characterization, it can be possible to build a gas sensor in the apparatus for collecting body fluid, and sensor of five categories such as a piezoelectric sensor, MOSFET (Metal-Oxide-Semiconductor Field Effect Transistor) sensor, an optical fiber sensor and a spectrometry sensor are fit into possible gas sensor. A disposable protector can be installed ahead of the gas sensor, through which air can be passed but liquid can be prevented from transmitting to protect the gas sensor and to increase durability.

In case of using a biosensor built in the apparatus for collecting and analyzing the body fluid, a disposable biosensor can be built in the collecting apparatus to measure particular constituent among constituents of body fluid (especially urine and blood). Several of constituents, such as Na, Cr, sugar, protein, urea, cortisol, pH etc. are measurable by using the biosensor and diversity of biosensor technique can be applicable to this. Biosensor capable of applying to the apparatus for collecting the body fluid comprises enzymatic sensor, immune sensor, DNA sensor, cellular sensor and laboratorial chip.

Figure 50:
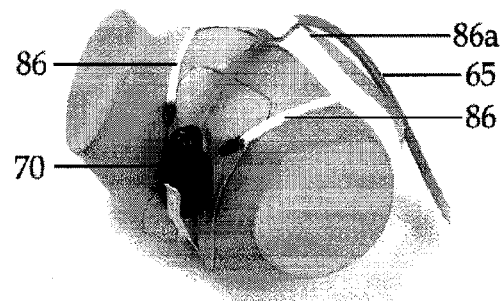
FIG. 50 is a perspective view showing another use embodiment of the apparatus for collecting body fluid according to the present invention.

Meanwhile, as a preferred embodiment for practicing the present invention, it can be possible to build a button (not shown) on the surface of analysis apparatus to draw out a hose of the total pipe automatically in case of omitting the total pipe 65 (FIGS. 32, 36 and 37) as well as using the total pipe, and such simple modification of structure is also within the scope of the present invention FIG. 50 is a perspective view showing one application embodiment of the apparatus for collecting the body fluid of the present invention, in which the collector case 70 is easily capable of wearing by connecting to the waist band 86a via the bidirectional fixed connecting band 86.

The invention claimed is:
1. An apparatus for collecting body fluid which consists essentially of:
   a body fluid collecting part; and
   a collecting case for collecting body fluid, said body fluid collecting part being detachably connected to said collecting case and constructed as a single body containing a body fluid absorbing passage, a cleansing passage and a cable passage containing an absorbing part and a sensor element, said absorbing part and sensor element being positioned to receive gravity flow from the body fluid collecting part and operatively articulated by a joint structure with said body fluid collecting part to facilitate the flexible positioning of the absorbing part and sensor element for receiving said body fluid.

2. The apparatus for collecting body fluid according to claim 1, wherein the joint structure of the body fluid collecting part and the adjacent elements are made of Teflon material.

3. The apparatus for collecting body fluid according to claim 1, wherein the body fluid absorbing passage and the absorbing part are fixed to each other by the formation of a pipe which extends through and penetrates the absorbing part, said absorbing part containing said sensor element extending therethrough.

4. The apparatus for collecting body fluid according to claim 1, wherein the joint system has a spherical or cylindrical configuration.

5. The apparatus for collecting body fluid according to claim 1, wherein multiple joint structures are constructed.

6. The apparatus for collecting body fluid according to claim 5, wherein the multiple joint structure provides rotational articulation in a plurality of directions.

7. The apparatus for collecting body fluid of claim 1, wherein the joint structure is positioned at each end of the body fluid collecting part.

8. An apparatus for collecting body fluid which consists essentially of:
a body fluid collecting part; and
a collecting case for collecting body fluid, said body fluid collecting part being detachably connected to said collecting case and constructed as a single body containing a body fluid absorbing passage, a cleansing passage and a cable passage containing an absorbing part and a sensor element, said absorbing part and sensor element being positioned to receive gravity flow from the body fluid collecting part,
wherein a gas sensor is installed in the body fluid collecting part, and a membrane, capable of transmitting air and not liquid, is operatively associated with the gas sensor to protect the gas sensor.

9. An apparatus for collecting body fluid which consists essentially of:
a body fluid collecting part; and
a collecting case for collecting body fluid, said body fluid collecting part being detachably connected to said collecting case and constructed as a single body containing a body fluid absorbing passage, a cleansing passage and a cable, wherein at least one sensing element is operatively associated with the collecting case which contains a plurality of absorbing holes which can be opened or closed by solenoid valves.

10. An apparatus for collecting body fluid which consists essentially of:
a body fluid collecting part;
a collecting case for collecting body fluid, said body fluid collecting part being detachably connected to said collecting case and constructed as a single body containing a body fluid absorbing passage, a cleansing passage and a cable passage containing an absorbing part and a sensor element, said absorbing part and sensor element being positioned to receive gravity flow from the body fluid collecting part; and
a locking device operatively associated with the body fluid collecting part and the collecting case to render these structures freely attachable and detachable.

* * * * *